United States Patent [19]

Vajda

[11] 4,283,176
[45] Aug. 11, 1981

[54] ENDODONTIC-PROSTHETIC STABILIZATION SYSTEM

[76] Inventor: Tibor T. Vajda, 92 Edgecliff Rd., Woollahra, N. S. W., Australia

[21] Appl. No.: 13,115

[22] Filed: Feb. 21, 1979

[30] Foreign Application Priority Data

Feb. 25, 1978 [AU] Australia ............... PD6099

[51] Int. Cl.³ ............................................ A61L 00/00
[52] U.S. Cl. ...................... 433/173; 433/220
[58] Field of Search ............... 433/173, 174, 175, 176, 433/194, 225, 193

[56] References Cited

U.S. PATENT DOCUMENTS

| 797,312 | 8/1905 | Osborn | 433/220 |
| 838,296 | 12/1906 | Best | 433/220 |
| 3,386,169 | 6/1968 | Scialom | 433/173 |
| 3,583,069 | 6/1971 | Edelman | 433/225 |

FOREIGN PATENT DOCUMENTS

92190 10/1922 Fed. Rep. of Germany ........... 433/194
894771 1/1945 France ..................... 433/220

*Primary Examiner*—Robert Peshock
*Attorney, Agent, or Firm*—Ladas & Parry

[57] ABSTRACT

An endodontic implant comprises a smooth, non-threaded partially tapered shank having an integral crown portion on which an artificial tooth crown or denture is supported. The shank is implanted in the root canal of a tooth stump and through its apex into the jawbone of a patient. The shank is preferably provided with two tapered sections with an intermediate section of constant diameter and is dimensioned so as to occupy the whole of a root canal cavity when implanted therein. Preferably the implants are used in pairs, rigidly connected by a bar device to which a denture can be removably attached. The system anchors mobile teeth and prevents root resorption caused by instability.

6 Claims, 2 Drawing Figures

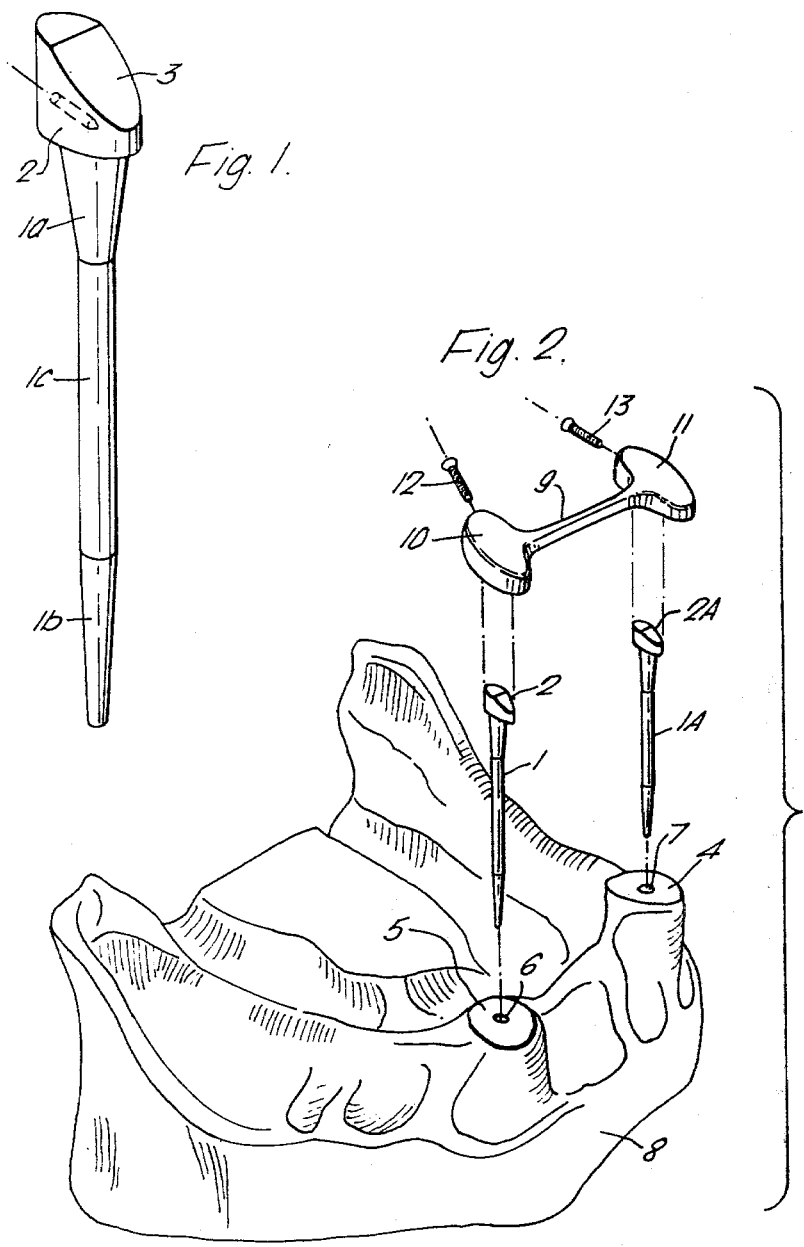

ENDODONTIC-PROSTHETIC STABILIZATION SYSTEM

FIELD OF THE INVENTION

This invention relates to a method for stabilising mobile teeth and particularly to an endodontic-prosthetic stabilisation system for preventing dentures from dislodgement.

BACKGROUND OF THE INVENTION

In the past, when a patient had lost most of his or her teeth, and where the remaining teeth are mobile, it was common practice to remove the remaining few teeth and to fit the patient with a complete mucosa-supported denture. This however had, and has, serious disadvantages for the patient.

Thus, the removal of all natural teeth provokes resorption of the roots which in turn causes a poor aesthetic effect, reduces the stability and retention of dentures and may cause psychological problems for the patient.

On the other hand, if most natural teeth have been lost, the forces acting on the remaining teeth, for example during mastication, are enormous, and eventually such teeth lose their alveolar bone support and become mobile and painful.

DESCRIPTION OF THE PRIOR ART

Various methods have been proposed for stabilising such remaining teeth to reduce or eliminate their mobility; however such previously proposed methods are not entirely satisfactory. For example it has been proposed to screw a threaded endodontic implant through the root canal of a tooth from which the coronal portion has been removed, into the jaw. A major problem caused by this type of implant arises however, because the screw action causes damage to the apex of the root canal and the adjacent bone resulting in a poor apical seal; this tends eventually to cause resorption of the root at that point leading to loss of stability and loss of alveolar bone support.

SUMMARY OF THE INVENTION

According to the present invention there is provided a system for stabilising teeth which avoids the problems mentioned above and moreover allows the firm retention of dentures in the mouth of a patient.

In accordance with the invention there is provided an endodontic implant having a smooth, non-threaded, partially tapered shank, and a crown portion integral with the shank, the shank being adapted for implantation through the root canal of a tooth stump and through the apex of that canal into the adjacent bone, the crown portion being adapted to support in a rigid manner an artificial tooth crown or means for supporting a denture.

PREFERRED FEATURES OF THE INVENTION

In a preferred embodiment of the invention, a system is provided comprising two or more such implants together with a bar attachment adapted to be screwed to the crown portion of such implants to provide an integral structure. In accordance with this preferred embodiment, the implants can be implanted in the jaw through the root canals of surviving natural teeth and then rigidly held in position horizontally by means of the bar screwed thereto. This permits rigid stabilisation of the teeth both vertically and horizontally, and also allows a denture to be clipped or otherwise secured to the bar.

It is not in itself novel to join two implants by means of a bar in order to secure a denture. However, the system according to the present invention provides a novel and highly efficient means for stabilising teeth and supporting dentures without the disadvangates of previously proposed methods.

Thus, it has been proposed previously to insert implants into two teeth, for example canine teeth, and to cement a joining bar across the stumps of those teeth. However, the forces acting on the tooth stumps, if these are relatively long, invariably lead to the stumps breaking off. On the other hand if the stumps are short, the cement joint is insufficiently strong to withstand the forces acting on it and it eventually gives way.

The system according to the present invention provides means for rigidly stabilising the two teeth without causing root resorption and such system can resist the constant forces resulting from mastication and from the application and removal of a denture to the bar. The screw connections between the bar and the crown portions of the implants are rigid and not subject to the weaknesses of cement joints. The whole system provides stabilising means of integral construction and consequent strength and resistance to masticatory and other forces.

The crown portion of the implants should be of such a size as to avoid undue horizontal stresses, i.e. they should not extend too far above the gingival margin; on the other hand it is necessary for them to be sufficiently long to provide adequate support for the screw-attached bar. In addition the crown portions are preferably shaped in such a way as to allow the setting of the artificial teeth in a natural manner to provide an aesthetic appearance. This can be achieved by bevelling the forward-facing portion of the crown portions in such a way that dentures are not forced forward beyond the mandibular ridge which would render the artificiality of the denture obvious and unaesthetic, and also reduce the stability of the denture.

The implants according to the present invention are preferably tapered so as to occupy substantially the whole of the tapered root canal of a tooth when implanted. In this way any movement of the implant within the canal is prevented and the danger of the apical seal being broken, with consequent risk of root resorption, is avoided.

Preferably the shank is provided with two tapered sections separated by a section of constant diameter. The lower tapered section is for convenience 16 mm long. This is to permit the use of standard internationally recognized endodontic instruments for root canal preparation which have a tapered section of this length. It will of course be appreciated that if instruments other than standard instruments were used, then the dimensions of the implant shank would have to be modified accordingly; it would of course be a pointless exercise to use special non-standard instruments.

Again to permit the use of standard instruments, the diameter of the upper point of the lower tapered section of the shank is 0.3 mm greater than the diameter of the lower end of the shank to conform with the taper of the standard instruments.

The upper tapered portion of the shank is designed to flare towards the crown portion to strengthen the joint between the crown portion and the shank and to prevent the crown portion breaking away, that is to preserve the integral construction of the implant. Conveniently the upper 3-6 mm, preferably 3 mm, of the shank may be so flared.

The crown portion is conveniently designed to extend approximately 2 millimeters above the gingival level. Although not critical, this height of the crown portion permits rigid application of the bar connection yet is sufficiently low to avoid the unduly excessive forces which act on conventional implants having relatively high crown portions.

A further significant advantage of the system according to the present invention resides in the fact that the bar attachment can be screwed to the implants by means of screws inserted horizontally. Certain implants have been proposed previously in which it has been suggested to attach bars to implants by means of screws passing through the bars and vertically down into the implant. Such an arrangement is unsatisfactory particularly because if a connection of adequate strength is to be achieved thereby, the crown portion with screw attachment must necessarily be so bulky as to lead to difficulties in producing an aesthetic form of denture.

The system according to the invention provides benefits to both patient and dentist which no previously described dental technique can offer. Thus, the patient is provided with a stable denture retaining means, while the dentist benefits from the simplicity of the system.

DESCRIPTION OF THE DRAWINGS

The invention is described by way of example only with particular reference to the accompanying drawings, FIGS. 1 and 2, in which FIG. 1 illustrates an implant according to the present invention while FIG. 2 represents schematically the manner in which the system according to the present invention is assembled in the mouth of a patient.

As shown in FIG. 1 an implant according to the invention comprises a non-threaded partially tapered shank 1 integrally provided with a crown portion 2. The shank is in fact provided with two tapered sections 1a and 1b, separated by constant diameter section 1c. The labial face of the crown portion is bevelled at 3 while the lingual portion is provided with a hole adapted to receive a screw (not shown).

In FIG. 2 the lower jaw of a patient is schematically illustrated and shows a patient having two remaining natural teeth 4 and 5 which have been ground down to the gingival level to expose the root canals 6 and 7.

Two implants 1 and 1A of the type illustrated in FIG. 1 are inserted through the root canals 6 and 7 respectively and are forced through the apex of the root canal into the jawbone 8. The lower tapered sections of the implants 1 and 1A are such that when inserted as aforesaid the tapered portions fully occupy the root canal spaces 6 and 7; of course the root canals are prepared beforehand and if necessary enlarged to accommodate the implants.

Following implantation, bar attachment 9 is then fitted over the crown portions 2 and 2A of the implants. Cup portions 10 and 11 of the bar attachment are formed so as to fit tightly over the crown portions 2 and 2A and are provided with screw threaded holes so as to align with the holes in crown portions 2 and 2A so that the implants 1 and 1A together with the bar attachment 9 can be integrally and rigidly joined together by means of screws 12 and 13.

Following fitting of the bar attachment, a denture plate can be clipped to the bar attachment so as to fit closely over the mandibular ridge of the patient. The denture would of course entirely obscure both the implants and the bar attachment from view.

It will of course be appreciated that the implants once permanently implanted must not be removed, yet the screw holes in the crown portions of the implants and the corresponding holes in the bar attachment must obviously be aligned precisely. This is achieved by inserting the implants in their proper position, then marking the exact position of the screw hole on the root surface. The implants are then removed and temporary implants (transfer shafts) are inserted and aligned with the mark on the root surface for impression taking purposes. An impression is then taken and removed with the transfer shafts from the patient's mouth. Thereafter the normal implants are again inserted in the patient's mouth, aligned with the mark, and permanently secured, that is cemented, into position. Thus, the implant is rigidly and permanently retained in position by frictional retention within the root canal and bone, and also by the cement joint. From the impression the bar attachment can be prepared having screw holes aligning precisely with those of the permanent implants.

I claim:

1. An endodontic implant for stabilizing a tooth which comprises a smooth non-threaded partially tapered shank having first and second ends, and a crown portion of circular cross-section integral with said first end of the shank, the shank comprising two tapered sections separated by a section of constant diameter, the first tapered section having a length of substantially 3 mm and tapering from the crown portion towards said constant diameter section and the second tapered section tapering from said constant diameter section towards said second end of the shank, the second tapered section having a length of substantially 16 mm and tapering constantly along its length such that its diameter where it meets said constant diameter section is substantially 0.3 mm greater than its diameter at said second end; the shank being adapted for implantation in a root canal of a tooth stump and being of a length such that the second tapered section passes through the apex of said root canal into the adjacent jawbone of a patient, whereby the tooth may be immobilized for supporting in a rigid manner an artificial tooth crown or a means for supporting a denture, the tapers of the implant shank being such that when implanted in the root canal of a tooth the whole of the root canal cavity is occupied by the shank.

2. A system comprising two or more implants according to claim 1 with a bar attachment adapted to be screwed to the crown portions of such implants, the bar attachment having cups which fit tightly over the crown portions of said implants, the cups being securable to the crown portions by means of screws passing horizontally through the bar attachment into transverse bores in the crown portions.

3. A system according to claim 2 in combination with a denture adapted to be attached thereto.

4. An implant according to claim 1 wherein the crown portion of the implant is bevelled on the labial side.

5. An implant according to claim 1 wherein the crown portion extends approximately 2 millimeters above the gingival level.

6. An implant according to claim 5 wherein a transverse screwed bore is provided in the lingual side of the crown for accommodating a screw in threaded engagement therewith for attachment of an artificial tooth crown or means for supporting a denture.

* * * * *